United States Patent [19]

Bertram et al.

[11] 4,073,945

[45] Feb. 14, 1978

[54] FODDER FOR COWS

[75] Inventors: Heidrun Bertram, Hanau; Rudolf Fahnenstich, Mombris; Heribert Offermanns; Herbert Tanner, both of Hanau, all of Germany

[73] Assignee: Deutsche Gold- und Silber-Scheideanstalt vormals Roessler, Frankfurt, Germany

[21] Appl. No.: 687,503

[22] Filed: May 18, 1976

[30] Foreign Application Priority Data

June 14, 1975 Germany .............................. 2526750

[51] Int. Cl.² ................................................ A23K 1/00
[52] U.S. Cl. ........................................ 426/2; 426/623; 426/636; 426/807; 260/534 L
[58] Field of Search .................. 426/2, 623, 636, 807; 260/534 L, 534 M, 482 R; 424/319

[56] References Cited

U.S. PATENT DOCUMENTS 2,833,821   5/1958   Hause ............................... 260/534 L

OTHER PUBLICATIONS

Migrdichian "Organic Synthesis", vol. 1, Reinhold Publishing Corp. 1957, pp. 148, 275 & 290.

Primary Examiner—R. B. Penland
Attorney, Agent, or Firm—Cushman, Darby & Cushman

[57] ABSTRACT

The calcium salts of mono-hydroxymethyl lysine and bis(hydroxymethyl) lysine are prepared by reacting lysine and formaldehyde in water containing calcium ions at a pH of at least 8 and at most 12.5. The compounds are useful as fodder for ruminants.

17 Claims, No Drawings

FODDER FOR COWS

The present invention is directed to the calcium salts of mono-hydroxymethyl lysine and bis(hydroxymethyl) lysine, a process for producing these compounds, and their use as fodder for ruminants.

Mono-hydroxymethyl lysine and bis(hydroxymethyl) lysine and their calcium salts have never been described. It is merely known that in the customary reaction of amines with formaldehyde for the production of N-hydroxymethyl derivatives of the amines in the case of lysine, there are formed cross-linked condensation and polymerization products, see Smith, J. Phys. Chem., Vol. 44 (1940), pages 874 to 880.

There has now been found a process for the production of the calcium salts of mono-hydroxymethyl lysine and bis (hydroxymethyl) lysine which comprises reacting lysine with formaldehyde in the presence of water and calcium ions at a pH of at least 8 and at most 12.5. In this manner, we have been able to recover the desired compounds in high yields and purity.

The reaction of lysine with formaldehyde according to the invention is preferably carried out in water. As the reaction medium, there can also be used mixtures of water and inert organic solvents, especially those which have unlimited miscibility with water, for example, mixtures of water with lower alcohols, e.g., methyl alcohol, ethyl alcohol and isopropyl alcohol, e.g., 80% water – 20% ethyl alcohol.

The reaction according to the invention takes place in the presence of calcium ions at a pH of at least 8 and at most 12.5. There can be employed either the calcium salt of lysine or lysine with addition of a calcium compound.

In the case that a mixture of lysine with a calcium compound is used, it is suitable to add the calcium compound in an, at least, stoichiometrical amount based on the lysine. The proportions of calcium compound to lysine can be selected to be of any size. However, it is generally suitable not to take more than 10 equivalents of calcium compound per mole of lysine. Preferably, 1.0 to 1.3 equivalents of calcium compound are used. As calcium compounds, there can be used those which give calcium ions in aqueous medium but do not give any disturbing side reactions with the lysine and formaldehyde. There can be used, for example, calcium salts such as calcium chloride, calcium nitrate, calcium acetate, calcium bromide, or calcium propionate or basic calcium compounds such as calcium oxide and calcium hydroxide. The calcium compounds are normally soluble in water having a pH of at least 8. If necessary, there is added to the reaction mixture a basic material, especially an alkali hydroxide, e.g., sodium hydroxide or potassium hydroxide, so that there is obtained a pH of at least 8.

The order in which the materials are mixed together can be widely varied. It is particularly advantageous to have present a solution of the calcium salt of lysine or a solution of a mixture of a calcium compound and lysine whose pH is adjusted to at least 8 and then to introduce the formaldehyde.

Whether there is formed the mono-hydroxymethyl compound or the bis(hydroxymethyl) compound depends on the proportions of lysine to formaldehyde. Suitably for the recovery of the mono-hydroxymethyl compound, there are used about equimolar amounts of lysine and formaldehyde, generally 0.8 to 1.3 moles, especially 1.0 to 1.2 moles of formaldehyde per mole of lysine. Upon adding more than 1.3 moles of formaldehyde per mole of lysine, there is formed to a considerable extent, besides the mono-hydroxymethyl compound, the bis(hydroxymethyl) compound and, upon addition of more than 1.6 moles of formaldehyde per mole of lysine, the bis(hydroxymethyl) compound predominates. To recover this compound, there are suitably used about two molar or larger amounts of formaldehyde, generally at least 1.8 moles, especially 2.0 to 2.3 moles of formaldehyde per mole of lysine.

The reaction temperature depends in a given case upon the types of reactants and solvents. Generally, the temperature is held between 0° and 60° C.

A preferred procedure is to react lysine, particularly in the form of lysine mono-hydrochloride, in aqueous medium first, in a given case, up to about 60° C., with 1.0 to 1.2 equivalents of calcium hydroxide, and then to react at a temperature up to about 30° C. with the desired amount of formaldehyde.*)

*) If lysine mono-hydrochloride is used, the amount of calcium hydroxide has to be doubled to neutralize the hydrochloric acid.

The reaction can be carried out with the racemate DL-lysine, as well as with the optical isomers D-lysine and L-lysine.

It is known to use aminoacids, especially the limiting aminoacids, as fodder additives, thereby to promote the utilization of the fodder by the animals and to strongly increase the growth and productivity of the animals. It has been shown that fattening poultry having a high methionine requirement and pigs especially need lysine. Therefore, these aminoacids are used to a great extent as feed additives in the concerned case.

However, the supplying of aminoacids as additives to fodder in the case of ruminants has proven ineffectual. The nutritional physiology of ruminants differs essentially from that of monogastric animals. As is known, ruminants have several stomachs. The first, by far the greatest stomach, the rumen, contains its own microflora of bacteria and protozoa which break down the added synthetic aminoacids, before they are utilizable for the animals (J. Animal Sci., Vol. 9 (1950), page 661; Vol. 10 (1951), pages 439–446 and 1052; Vol. 14 (1955), pages 132–136).

However, the aminoacids are effective if they are infused directly into the abomasum, for example, as aqueous solution (Reis, Australian J. Biol., Sci., Vol. 16 (1963), pages 218–230, and Reis, Australian J. Biol. Sci., Vol. 17 (1964), pages 532–547). Such a procedure is expensive and useful only for experimental purposes.

It is also known to add derivatives of methionine, namely, N-acyl methionine and N-hydroxymethyl methionine, as additives for fodder for ruminants and, thereby, to produce a substantial increase in the growth and productivity in the animals, for example, in the growth of wool in sheep (see Fahnenstich, German Offenlegungsschrift No. 2,205,210, and related Fahnenstich U.S. application Ser. No. 330,110, filed Feb. 6, 1973, and Bertram, German Offenlegungsschrift No. 2,307,836 and related Bertram U.S. application Ser. No. 441,983, filed Feb. 13, 1974). The use of these compounds, however, has proven difficult in many cases because the animals, apparently because of the taste and odor, only eat them unwillingly.

It has now been found that the calcium salt of mono-hydroxymethyl L-lysine and the calcium salt of bis (hydroxymethyl) L-lysine, as well as mixtures of these salts, are outstandingly suitable as a foddering agent for ruminants. The compounds are as good as free from odor and taste and can, therefore, be eaten by the animals without anything further. Typical ruminants which can be given the calcium salts of the N-methylol lysines, are sheep, goats, cattle (both beef and dairy cattle), deer, antelope and elk. The animals can also be fed the calcium salts of racemic N-methylol lysines.

The salts or their mixtures can be directly fed to the ruminants. Generally, they are used in conventional feeds or mixed feeds, or added to premixtures such as vitamin and mineral mixtures, or with feed-grade urea. Conventional fodder can be used, e.g., grass, oat shell meal, alfalfa, silage, corn, grain sorghum, oats, rice, rice meal, soybean meal, wheat millfeed, gluten meal, cottonseed meal, hay, barley feed, barley mixed feed, distillers dried grain, peanut meal, dried molasses beet pulp, etc.

The amount of the calcium salts of the hydroxymethyl lysine or their mixtures can be within a wide range. Generally, however, the amount of the salts or their mixtures added to the feed, based on the entire amount of feed (on a dry basis) supplied in one day should be about 0.01 to 5%, especially about 0.02 to 1.0% by weight.

Unless otherwise indicated, all percentages are by weight.

EXAMPLE 1

Process For the Production of the Calcium Salts of the Hydroxymethyl - Lysines a.

182.7 grams of L-lysine mono-hydrochloride and 74.1 grams of calcium hydroxide were dissolved in 1000 ml. of water at 40° C. After cooling the solution to 25° C., in the course of 10 minutes, there were added, dropwise with stirring, 81.2 grams of an aqueous formaldehyde solution containing 37 weight percent formaldehyde. The mixture was stirred for an additional 3 hours at 25° C. and then cooled to 5° C.. Thereupon, the calcium salt of mono-hydroxymethyl-L-lysine was separated out as crystals. They were filtered-off with suction, washed with cold water, and then dried at 50° to 70° C. at a pressure of 2 millibars.

Element Analysis

|  | C | H | N | O | Ca |
|---|---|---|---|---|---|
| Calculated (%) | 43.06 | 7.74 | 14.34 | 24.58 | 10.26 |
| Found (%) | 43.19 | 7.50 | 14.60 | 24.51 | 10.41 |

Bound Formaldehyde (Photometric determination of the formaldehyde set free by acidification of the product and colored by means of chromotropic acid according to Zeitschrift fur Anal. Chemie, Vol. 110, (1937), page 22).

Calculated 15.38%; Found 15.25%

Bound Lysine (Determination of the lysine set free by acidification of the product by means of ninhydrin).

Calculated 74.36%; Found 73.61%

The yield of the calcium salt of the mono-hydroxymethyl-L-lysine amounted to 145 grams, corresponding to 73.9%, based on the L-lysine added. Upon concentration of the mother liquor under reduced pressure, there were recovered 22.8 grams of a less-pure product.

b.

182.7 grams of L-lysine mono-hydrochloride and 74.1 grams of calcium hydroxide were dissolved in 2500 ml. of water at 40° C. After cooling the solution to 25° C., there were added, dropwise with stirring, in the course of 15 minutes, 162.4 grams of an aqueous formaldehyde solution having a formaldehyde content of 37 weight percent. The mixture was stirred a further 3 hours at 25° C. and then cooled to 5° C. Thereupon, the calcium salt of bis(hydroxymethyl)-L-lysine separated out as crystals. They were filtered off under suction, washed with a little cold water, and then dried at 50° C. at a pressure of 2 millibars.

Element Analysis

|  | C | H | N | O | Ca |
|---|---|---|---|---|---|
| Calculated (%) | 42.65 | 7.61 | 12.44 | 28.41 | 8.90 |
| Found (%) | 42.21 | 7.50 | 12.08 | 28.78 | 9.01 |

Bound Formaldehyde

Calculated 26.66%; Found 25.98%

Bound Lysine

Calculated 64.44%; Found 65.12%

The yield of the calcium salt of bis(hydroxymethyl)-L-lysine amounted to 167 grams, corresponding to 73.8%, based on the L-lysine employed. Upon concentration of the mother liquor under reduced pressure, there were recovered a further 25.4 grams of a less-pure product.

EXAMPLE 2

Use of the Calcium Salts of the Hydroxymethyl Lysines as Fodder

As test animals, there were used 16 merino sheep in four groups, each containing four animals. As base fodder, there was dispensed per animal per day, depending on the age of the animals, 800 to 1000 grams of a mixture of 60 weight percent corn and 40 weight percent barley, with addition of a mineral mixture, as well as straw, in an unlimited amount. The animals were fed in the groups successively for two periods of five days each as follows:

Group I, Animals 1 to 4, only base fodder;
Group II, Animals 5 to 8, addition of 0.25 weight % L-lysine mono-hydrochloride to the base fodder;
Group III, Animals 9 to 12, addition of 0.35 weight % of the calcium salt of the bis(hydroxymethyl)-L-lysine to the base fodder;
Group IV, Animals 13 to 16, addition of 0.03 weight % of the calcium salt of the monohydroxymethyl-L-lysine to the base fodder.

In each case, the increase in the amount of nitrogen was measured.

Nitrogen Increase (Determined according to Andreas Hork, "Vergleichende Ernahrungslehre des Menschen und seiner Haustiere", Gustav Fischer Verlag Stuttgart, 1966, pages 834 et seq. )

|  | Nitrogen Increase Grams of Nitrogen per animal per day | | |
| --- | --- | --- | --- |
|  | First 5 days | Second 5 days | Average Value of the 10 days |
| Group I Animal 1 | −3.0 | −5.5 | −4.3 |
| 2 | 3.9 | 4.3 | 4.1 |
| 3 | 2.4 | 5.4 | 3.9 |
| 4 | 3.8 | 1.1 | 2.5 |
| Group Average | 1.8 | 1.3 | 1.6 |
| Group II Animal 1 | 3.9 | 4.1 | 4.0 |
| 2 | 3.1 | 3.3 | 3.2 |
| 3 | 2.5 | 2.4 | 2.5 |
| 4 | 3.0 | 3.4 | 3.2 |
| Group Average | 3.1 | 3.3 | 3.2 |
| Group III Animal 1 | 11.0 | 16.3 | 13.7 |
| 2 | 14.5 | 14.9 | 14.7 |
| 3 | 10.6 | 13.2 | 11.9 |
| 4 | 12.4 | 14.1 | 13.3 |
| Group Average | 12.1 | 14.6 | 13.4 |
| Group IV Animal 1 | 13.1 | 14.2 | 13.7 |
| 2 | 15.7 | 17.1 | 16.4 |
| 3 | 17.9 | 18.8 | 18.3 |
| 4 | 14.8 | 16.4 | 15.6 |
| Group Average | 15.4 | 16.6 | 16.0 |

The process can comprise, consist essentially of, or consist of the steps set forth.

What is claimed is:

1. The calcium salts of mono and bis hydroxymethyl derivatives of lysine.

2. The salt of claim 1 which is the calcium salt of mono-hydroxymethyl lysine.

3. The salt of claim 2 in crystalline form.

4. The salt of claim 2 which is the calcium salt of mono-hydroxymethyl-L-lysine.

5. The salt of claim 1 which is the calcium salt of bis(hydroxymethyl) lysine.

6. The salt of claim 5 in crystalline form.

7. The salt of claim 5 which is the calcium salt of bis(hydroxymethyl)-L-lysine.

8. A process for the production of a calcium salt of a mono or bis hydroxymethyl derivative of lysine comprising reacting lysine with formaldehyde in the presence of water and calcium ions at a pH of at least 8 and at most 12.5.

9. A process according to claim 8 wherein there are employed 0.8 to 2.3 moles of formaldehyde per mole of lysine.

10. A process according to claim 9 there are employed 1.0 to 1.2 moles of formaldehyde per mole of lysine and there is obtained the calcium salt of mono-hydroxymethyl lysine.

11. A process according to claim 9 wherein there are employed 2.0 to 2.3 moles of formaldehyde per mole of lysine and there is obtained the calcium salt of bis(hydroxymethyl) lysine.

12. A process according to claim 8 including the additional step of recovering a member of the group consisting of the calcium salt of mono-hydroxymethyl lysine and bis (hydroxymethyl) lysine.

13. A process according to claim 12 comprising recovering said salt in crystalline form.

14. A process comprising feeding to a ruminant a calcium salt made according to claim 8 in an amount of 0.01 to 5 weight percent of the total daily fodder said salt being the calcium salt of (1) mono-hydroxymethyl-L-lysine; or (2) bis(hydroxymethyl)-L-lysine.

15. A fodder for a ruminant comprising a calcium salt made according to claim 8, said salt being the calcium salt of (1) mono-hydroxymethyl-L-lysine; or (2) bis(hydroxymethyl)-L-lysine, said calcium salt being 0.01 to 5 weight percent of the total daily fodder.

16. A process according to claim 14 wherein the ruminant is a sheep.

17. A process according to claim 14 wherein the ruminants are sheep, cattle or goats.

* * * * *